United States Patent
Spear et al.

(10) Patent No.: US 10,204,320 B2
(45) Date of Patent: Feb. 12, 2019

(54) INTEGRATED SYSTEM FOR PRODUCING PROCEDURAL DATA CHANGE SETS COMMUNICATED TO CLIENT DEVICES

(71) Applicant: TeleTracking Technologies, Inc., Pittsburgh, PA (US)

(72) Inventors: Steve Spear, Lindstrom, MN (US); Toni D. Morrison, Pittsburgh, PA (US); Corey Paracca, South Park, PA (US); Ann M. Della Porta, East Norriton, PA (US)

(73) Assignee: TeleTracking Technologies, Inc., Pittsburgh, PA (US)

( * ) Notice: Subject to any disclaimer, the term of this patent is extended or adjusted under 35 U.S.C. 154(b) by 95 days.

(21) Appl. No.: 15/339,185

(22) Filed: Oct. 31, 2016

(65) Prior Publication Data
US 2017/0046661 A1  Feb. 16, 2017

Related U.S. Application Data

(63) Continuation-in-part of application No. 15/142,712, filed on Apr. 29, 2016.
(Continued)

(51) Int. Cl.
*G06F 15/16* (2006.01)
*G06Q 10/10* (2012.01)
(Continued)

(52) U.S. Cl.
CPC ....... *G06Q 10/1095* (2013.01); *G06F 3/0488* (2013.01); *G06F 3/04842* (2013.01);
(Continued)

(58) Field of Classification Search
CPC .... G06Q 10/1095; G06Q 10/06; G06Q 10/10; G06F 3/04842; G06F 3/0488
(Continued)

(56) References Cited

U.S. PATENT DOCUMENTS 6,957,188 B1 *  10/2005  Dellevi .......... G06Q 10/063112
                                             705/7.14
2003/0018509 A1 *  1/2003  Ossip .................... G06Q 10/06
                                             705/7.16
(Continued)

OTHER PUBLICATIONS

Extended Search Report for European Patent Application No. EP17195403, dated Oct. 30, 2017, 2 pages, The Hague, Netherlands.
(Continued)

*Primary Examiner* — Philip B Tran
(74) *Attorney, Agent, or Firm* — Ference & Associates LLC (57) ABSTRACT

An embodiment provides a method, including: communicating with a server to obtain change data derived from a set of event data; said set of event data comprising timestamped event data permitting calculation of a delta with respect to a scheduling milestone; identifying, using a processor, a display element impacted by the change data; and updating, using the processor, the display element according to the change data; said updating comprising changing a color of a display graphic in a schedule view to visually indicate the change data. Other embodiments are described and claimed.

20 Claims, 8 Drawing Sheets

Related U.S. Application Data (60) Provisional application No. 62/155,245, filed on Apr. 30, 2015.

(51) Int. Cl.
*G06F 3/0484* (2013.01)
*G06F 3/0488* (2013.01)
*H04L 29/08* (2006.01)
*H04L 29/06* (2006.01)
*G06Q 10/06* (2012.01)
*G16H 10/60* (2018.01)
*G16H 40/20* (2018.01)

(52) U.S. Cl.
CPC ............ *G06Q 10/06* (2013.01); *G06Q 10/10* (2013.01); *G16H 10/60* (2018.01); *G16H 40/20* (2018.01); *H04L 67/02* (2013.01); *H04L 67/10* (2013.01); *H04L 67/36* (2013.01); *H04L 67/42* (2013.01)

(58) Field of Classification Search
USPC .................................................. 709/203, 223
See application file for complete search history.

(56) References Cited

U.S. PATENT DOCUMENTS

| | | | |
|---|---|---|---|
| 2005/0177407 A1* | 8/2005 | Barni | G06Q 10/06 705/7.14 |
| 2006/0053035 A1* | 3/2006 | Eisenberg | G16H 40/20 705/2 |
| 2008/0221924 A1 | 9/2008 | Ilkin | |
| 2010/0306017 A1* | 12/2010 | Dreyfuss | G06Q 10/06 705/7.16 |
| 2011/0153352 A1* | 6/2011 | Semian | G06Q 10/06 705/2 |
| 2014/0058779 A1 | 2/2014 | Kissoon et al. | |
| 2014/0164011 A1 | 6/2014 | Guelich et al. | |
| 2015/0310659 A1 | 10/2015 | Spear et al. | |

OTHER PUBLICATIONS

Search Report for European Patent Application No. EP16167624, dated Aug. 11, 2016, 2 pages, The Hague, Netherlands.

Mesbah et al., "A component- and push-based architectural style for AJAX applications", Journal of Systems and Software, Dec. 1, 2008, 16 pages, Elsevier North Holland, New York, New York.

"Version Control with Subversion, 2nd Edition", Fundamental Concepts, Sep. 23, 2008, 6 pages, O'Reilly Media, Inc.

Carlyle, B., "Semantic Delta Encoding with HTTP draft-carlyle-sem-delta-encoding-00", Internet Engineering Task Force, IETF; Standard Working Draft, Internet Society (ISOC) 4, Rue Des Falaises CH-1205 Geneva, Switzerland, Jun. 30, 2012, pp. 1-19.

Collins-Sussman et al., "Chapter 1, Chapter 2" in "Version Control with Subversion, 2nd Edition", O'Reilly Media Inc., Sep. 23, 2008, pp. 1-46.

* cited by examiner

INTEGRATED SYSTEM FOR PRODUCING PROCEDURAL DATA CHANGE SETS COMMUNICATED TO CLIENT DEVICES

CROSS REFERENCE TO RELATED APPLICATIONS

This application is a continuation-in-part of U.S. patent application Ser. No. 15/142,712, filed on Apr. 29, 2016, which in turn claims priority to U.S. Provisional Application Ser. No. 62/155,245, filed on Apr. 30, 2015; the contents of each of these applications are incorporated by reference herein.

BACKGROUND

Disparate client devices, e.g., smart phones, computer work terminals, smart-TVs or other displays, etc., need to be apprised of real-time status changes in workflows. Conventional techniques for accomplishing this include making phone calls or otherwise communicating change information directly. Moreover, some conventional approaches include manual entries into stand alone systems, e.g., provided at a work station, manually writing updates to a whiteboard, etc.

Managing workflows however requires a solution that can maximize both throughput and the fixed costs attributed to the unit of operation. Most of existing inefficiencies in these areas are related to poor communication and communication of data that is not transparent to the interdisciplinary teams working to support the workflow.

Existing electronic records and static scheduling programs are of value; however, the information they document is often historic, static and (if updated) not provided or communicated in real time. Thus, existing systems do not anticipate schedule changes and/or track the workflow and procedural milestone processes in real-time, e.g., on the day of a procedure. Such difficulties are complicated by the modular nature of electronic records and scheduling systems, i.e., these modular units are traditionally not designed to operate in a coordinated fashion. Electronic records, static scheduling programs and the like thus lack any real time transparency to all events relating to a particular workflow.

BRIEF SUMMARY

In summary, one embodiment provides a method, comprising: communicating with a server to obtain change data derived from a set of event data; said set of event data comprising timestamped event data permitting calculation of a delta with respect to a scheduling milestone; identifying, using a processor, a display element impacted by the change data; and updating, using the processor, the display element according to the change data; said updating comprising changing a color of a display graphic in a schedule view to visually indicate the change data.

Another embodiment provides a system, comprising: a memory storing instructions; a processor configured to execute the instructions to: communicate with a server to obtain change data derived from a set of event data; said set of event data comprising timestamped event data permitting calculation of a delta with respect to a scheduling milestone; identify a display element impacted by the change data; and update the display element according to the change data; said update comprising changing a color of a display graphic in a schedule view to visually indicate the change data.

A further embodiment provides a program product, comprising: a storage device having code stored therein that is executable by a processor, the code comprising: code that communicates with a server to obtain change data derived from a set of event data; said set of event data comprising timestamped event data permitting calculation of a delta with respect to a scheduling milestone; code that identifies, using a processor, a display element impacted by the change data; and code that updates, using the processor, the display element according to the change data; said update comprising changing a color of a display graphic in a schedule view to visually indicate the change data.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

BRIEF DESCRIPTION OF THE SEVERAL VIEWS OF THE DRAWINGS

FIG. 6 illustrates an example user interface displaying gap change information on a client device display.

DETAILED DESCRIPTION

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well known structures, materials, or operations are not shown or described in detail to avoid obfuscation.

An embodiment provides centrally managed workflow service, implemented for example in a server or servers that are connected to other, existing systems (e.g., patient or asset RTLS tracking systems, bed management systems, scheduling systems, etc.) or that operate in a stand-alone implementation. A central service paradigm offers coordinated communication to various staff devices and permits a central location that may be updated with change information that is distributed to various clients, e.g., mobile devices, client workstations or other linked systems of devices.

In an embodiment, tracking data is provided to a central service (e.g., implemented in a server) that permits comparison to predetermined timing data to determine a change set or change information. For example, the tracking data may indicate that a service or segment thereof has ended or has been completed early, and thus more time is available in a preexisting schedule. Likewise, the tracking data may indicate that a service or segment thereof has not ended or has not been completed on time, and thus less time is available for in a preexisting schedule.

In an embodiment, a screen or view approach is provided such that, for a given service, e.g., a clinic, a series or set of views offers staff, management and others visible data and information that permits real time tracking and progress information correlated to tracking information regarding initiation of a service, tracking information as the service progresses, and tracking information about the end of a service or transition to another service, e.g., another clinic. This tracking data may be used to compare to predetermined timing data such that gaps and/or overlaps in service segments are determined in real-time or near real time. This allows an embodiment to update the graphical user interfaces of client devices to apprise users thereof of delays (causing potential scheduling overlaps), services or segments thereof ending early (causing gaps), and/or apprise users of potential alternate scheduling options for optimizing a workflow.

The quality of the tracking data and change information is improved via central management, as various sources may be used to update the views or screens, in real time, as accessed by a central manager. By way of example, a central server may access existing scheduling data and electronic medical record (EMR) data to initially populate a screen or view, e.g., a screen or view offering a view of the day's schedule, including the scheduled procedures, the units or areas to which they are assigned, and when, the staff assigned to work within the units, and areas etc.

By implementing a centrally coordinated system paradigm, an embodiment facilitates coordination and distribution of the best available information in a timely fashion. Thus, an embodiment may update initially scheduled times, communicate delays or other information (e.g., alerts) to the various views or screens such that users may be apprised of updates in real time. This facilitates efficient use of resources and keeps staff, managers and others apprised of the actual progression of the workflow(s).

The screens or views offer the client devices the ability to view and in some cases update (e.g., depending on the user's role) the information that is currently available in the system. By way of example, a staff member currently in a preoperative care area may provide an update (e.g., via mobile application, desktop web browser interface or the like) such that a delay in the patient's progress to the operating room is communicated to the central manager. The central manager in turn may provide update(s), e.g., notification of the delay, to other devices, e.g., by communicating information allowing the screens or views of the client devices to be changed.

The screens or views are implemented with specific functionality. For example, a screen or view allows a user to be apprised of delays (detected manually, e.g., by staff input, or automatically, e.g., by missing RLTS milestone data, etc.) in a view via use of a timer icon. Other icons and supporting functionality are provided, and these may be customized according to the workflow in question. A screen or view also permits authorized users to implement changes to the workflow (e.g., indicate delays, indicate early completion of various tasks, indicate changes in the availability of certain staff members, indicate changes in the availability of certain units, areas or pods, etc.). This may be implemented via use of a drag and drop or other interface functionality supported by executable code associated with the screen or view.

Given the centrally managed approach described herein, an embodiment facilitates generation of reports that leverage the most up to date, accurate and granular data available. Thus, an embodiment may be preprogrammed to generate standard reports from EMR data, scheduled data, and/or actual workflow completion data, and may be customized to access data of the centrally managed systems and/or other systems to generate custom reports.

An embodiment enhances EMR and other systems (e.g., scheduling, real time tracking, etc.) by integrating their data into a series of useful screens or views for particular health care staff members. For example, an embodiment takes an anticipated schedule and tracks a workflow and procedural milestone processes in real-time on the day of the procedure. This provides real time transparency to all events relating to the workflow. By communicating activities as they are happening, an embodiment supports effective in-the-moment decision making to minimize the many unanticipated changes that invariably occur throughout the workflow and provides staff the ability to make changes. An embodiment therefore provides an integrated system similar to an "air traffic control system"—one that can not only locate and track all the elements involved in the workflow. Additionally, an embodiment may use real time data to highlight (e.g., visually) anticipated gaps, overlaps or other status indicators that affect the workflow.

An embodiment provides a procedural throughput solution that enables enhanced throughput and increases utilization of high touch, high volume areas.

An embodiment may be integrated as a module for management system (e.g., included as a module along with modules for pre-admission tracking, electronic bed board, transport tracking, and/or bed tracking) or an embodiment may be provided as a stand-alone procedural throughput system. An embodiment works collaboratively with the various aspects of the existing system(s) to provide a comprehensive end-to-end picture of the workflow continuum within the system.

An embodiment is effective in higher complexity workflows. These procedures can entail discrete or multiple workflows and are typically scheduled in advance.

An embodiment may also be employed for visualizing and managing medium complexity workflows. The medium complexity areas may have multiple procedure rooms or areas with associated equipment varying by procedure type.

Some medium complexity areas may have preparation locations used before the procedure and recovery locations for after the procedure.

An embodiment may be employed as well as in low complexity workflows. These low complexity areas provide in and out visits and/or procedures. These low complexity areas often do not require the coordination of a large number of staff and may have only one or two tracked procedure steps (e.g., start and complete). Procedure staff for such services may be scheduled or assigned on an ad-hoc basis or may not require individual staff to be assigned unless a specific issue arises. Coordination of such low complexity services itself becomes complex throughout a larger facility with numerous such workflows that interact with higher workflow areas.

In an embodiment, the system is integrated with a real time location service (RTLS) for automated tracking and updates and therefore may be integrated with various modules or systems, e.g., a transport tracking system. This facilitates automated information influx into the central system and to the various screens or views of the client devices.

An embodiment also provides automated production of standard reports, whereas previously users had to create their own reports using custom views and techniques. The reports may be based on and reflect data gathered from various systems. For example, a report may be automatically generated to show average throughput times for various areas, summarize delay points, and highlight problem areas for improvement, etc. Additionally, an embodiment includes standard templates and reports for facilities, in addition to the already existing templates that may be provided with the system.

The illustrated example embodiments will be best understood by reference to the figures. The following description is intended only by way of example, and simply illustrates certain example embodiments.

Figure 1:
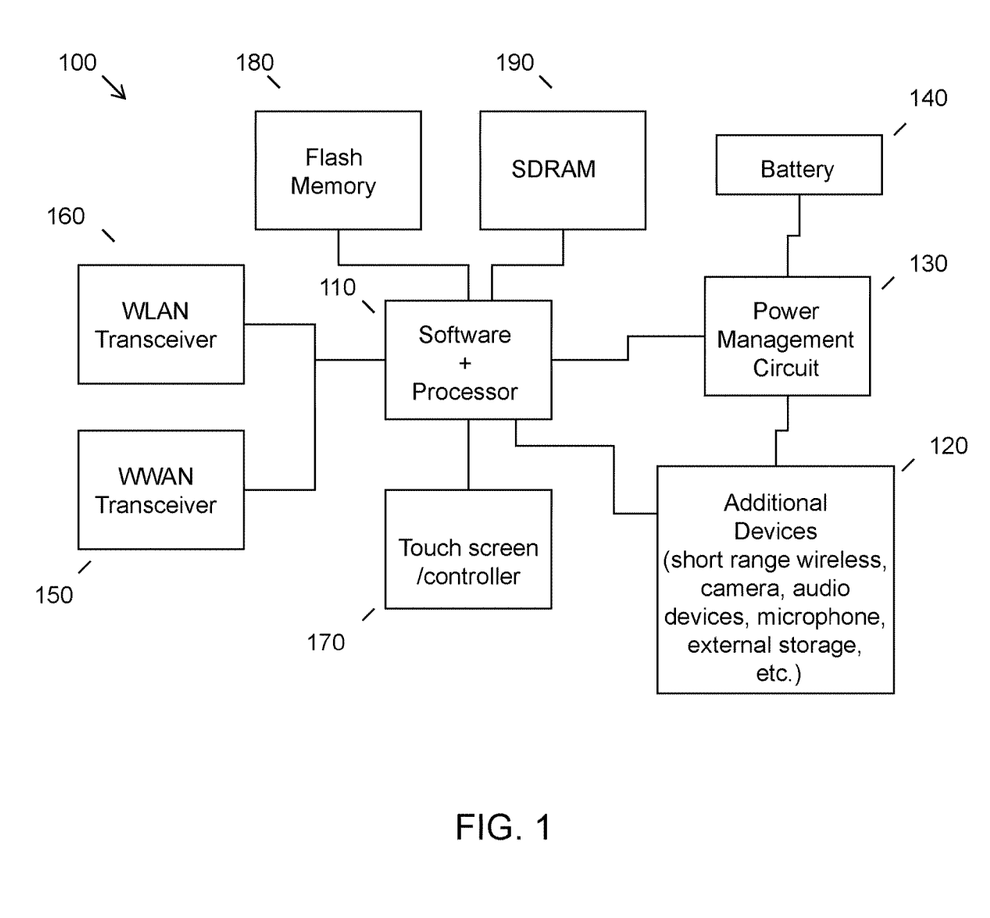
FIG. 1 illustrates an example of information handling device circuitry.

While various other circuits, circuitry or components may be utilized in information handling devices, with regard to system on chip circuitry, an example illustrated in FIG. 1 includes a system 100 on a chip or circuit design found for example in tablets, smart phones or other mobile computing platforms. Software and processor(s) are combined in a single chip or circuit 110. Processors comprise internal arithmetic units, registers, cache memory, busses, I/O ports, etc., as is well known in the art. Internal busses and the like depend on different vendors, but essentially all the peripheral devices (120) may attach to a single chip or circuit 110. The circuitry 100 combines the processor, memory control, and I/O controller hub all into a single chip 110. Also, a system 100 of this type does not typically use SATA or PCI or LPC. Common interfaces, for example, include SDIO and I2C.

There are power management chip(s) or circuit(s) 130, e.g., a battery management unit, BMU, which manage power as supplied, for example, via a rechargeable battery 140, which may be recharged by a connection to a power source (not shown). In at least one design, a single chip or circuit, such as 110, is used to supply BIOS like functionality and DRAM memory.

System 100 typically includes one or more of a WWAN transceiver 150 and a WLAN transceiver 160 for connecting to various networks, such as telecommunications networks and wireless Internet devices, e.g., access points. Additional devices 120 may be included, for example external storage. Commonly, system 100 will include a touch screen 170 for data input and display/rendering. System 100 also typically includes various memory devices, for example flash memory 180 and SDRAM 190.

Information handling device circuitry, as for example outlined in FIG. 1, may be used in mobile client devices such as a smart phone that provide and receive updates or in a server or system that coordinates with various systems, i.e., receiving various change information and coordinating the communication of the same. As will be appreciated by one having ordinary skill in the art, other circuitry or additional circuitry from that outlined in the example of FIG. 1 may be employed in various electronic devices that are used in whole or in part to implement the systems, methods and products of the various embodiments described herein.

Figure 2:
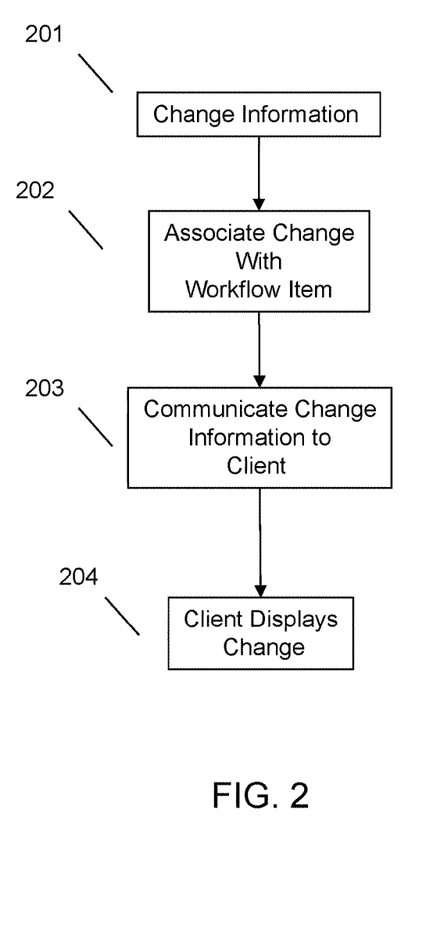
FIG. 2 illustrates an example method of communicating change data for a client screen or view.

Referring to FIG. 2, an example of change information is input to a central server at 201. This may correspond for example to a staff member updating information, e.g., at a workstation or via a mobile application, e.g., a staff member checking into a particular room, data obtained from an RTLS system, etc. Additional sources of change information may include but are not necessarily limited to data from an existing or legacy system, e.g., a scheduling system, an EMR system, etc.

At the central server, the change information is associated with appropriate workflow items at 202. For example, staff member check in information may be used to identify the staff member's workflow, and thus other users, and/or data elements, e.g., icons, panels, etc., such that these may be updated with the change information.

At 203, an embodiment communicates the change information to the appropriate application(s) in order to provide real time updates. This communication may include animation information or may be a simple identifier of the element(s) to be changed, as well as addressing information for the destination(s), e.g., mobile device identifiers, workstation identifiers, identification of a display screen in a lobby, etc.

Having an indication of a change, at 204 the recipient of the change information, e.g., a mobile application, a staff member work station, a display such as a television or smart TV, etc., may update the view or screen provided thereby, e.g., animate the change using this indication. This may be implemented in a variety of ways. For example, the change information communicated from the server (either via a pushing or pulling mechanism) may include animation information. Alternatively or additionally, the local (receiving) client application may have predetermined update (e.g., animation, color change, or other update information) that is triggered by the indication provided by the change information. For example, a predetermined change may be included in a template that is populated with change information, with the change to the display or view being executed in a local client action. Thus, a mobile application or web browser operating on a local (receiving) client may quickly apprise the user of the relevant change that has taken place, facilitating better management of the workflow items.

Figure 3:
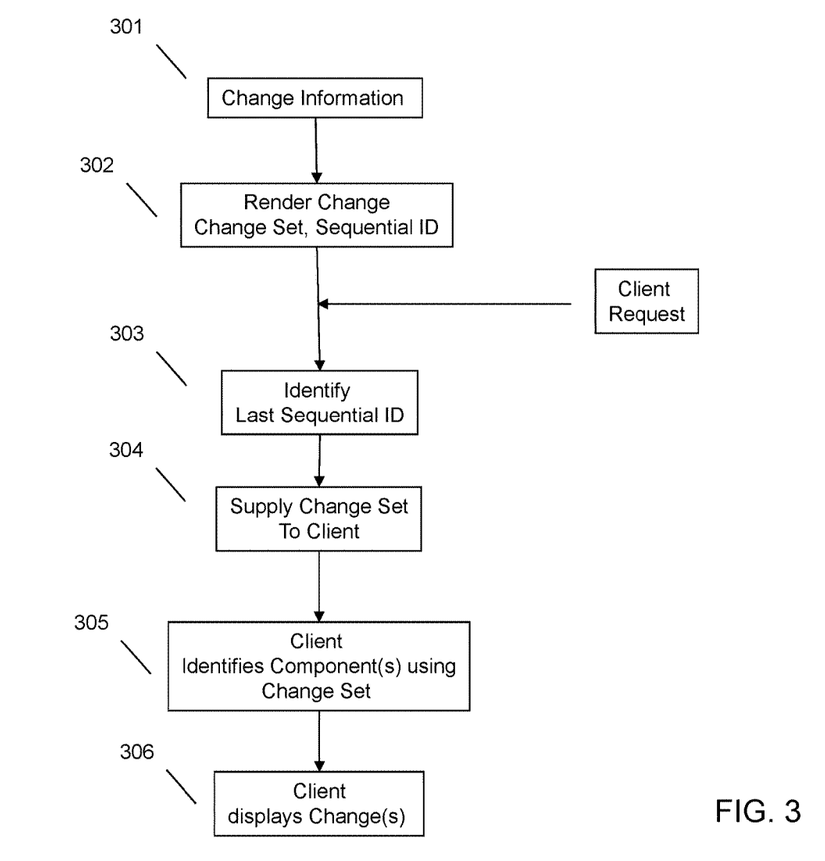
FIG. 3 illustrates an example method of preparing, communicating and implementing changes for a client screen or view.

By way of non-limiting example, and referring to FIG. 3, in an example mobile client/server implementation, the changes or workflow updates referred to herein, may be provided as follows. A universal interface virtual machine (UIVM) server (e.g., Orchestrate™ application server) receives information from the Orchestrate™ system, e.g., a server of a linked system, a workstation, a mobile client, etc., at 301. This information may be used by a UIVM server at 302 to render a change set and associate the change set with a sequential ID, which may be placed into a cache.

On an incoming request, e.g., as for example communicated by an Orchestrate™ application operating on a mobile client, a request for an updated web browser page, according to a policy (e.g., update policy), etc., the change set from UIVM server (e.g., via regular polling or when user opens application to see changes) may supply or identify the last sequence ID it received at 303.

The UIVM server may then respond at 304 with the change set required by the client to make it consistent with the underlying UIVM data store. The client may then use the change set at 305 to identify the GUI component(s) or other view components that are to be changed, and thereafter implement the changes at 306 (e.g. addition, deletion, or modification of GUI components, icons or other display graphics, etc.).

Figure 4:
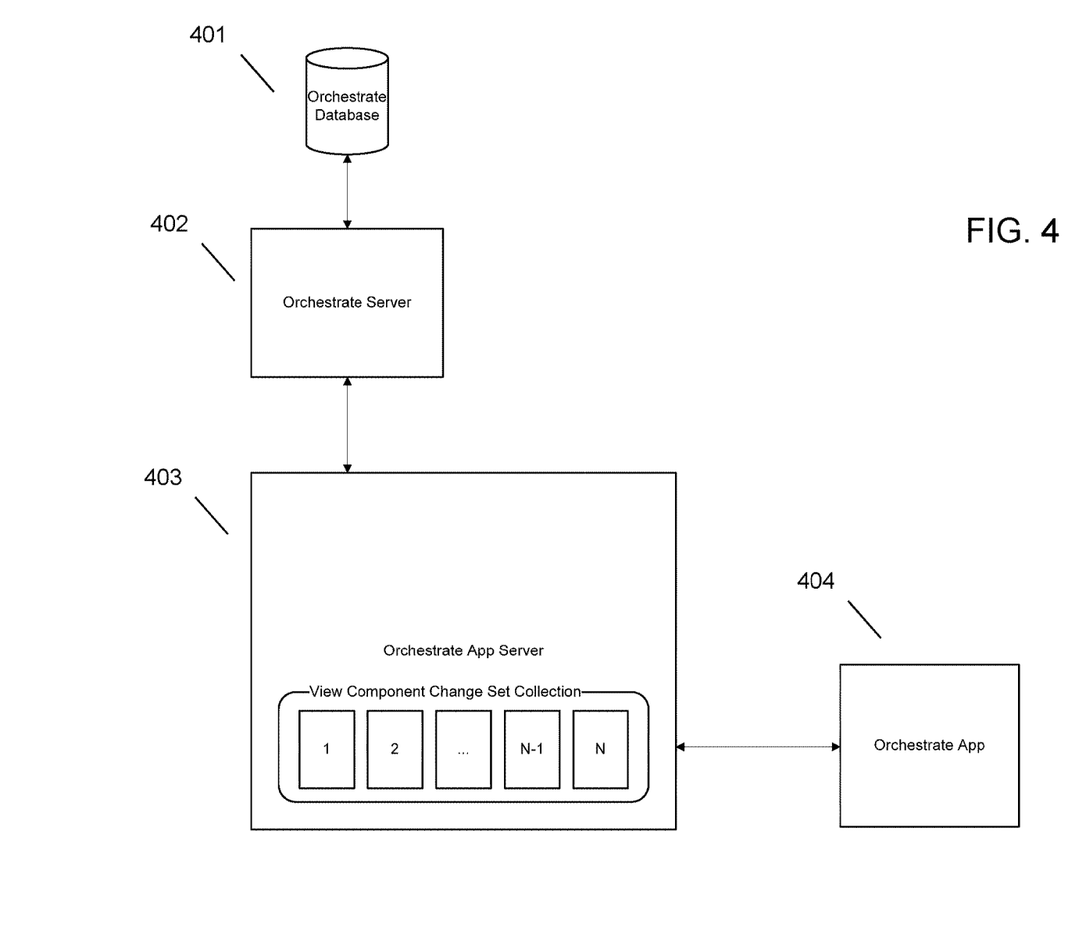
FIG. 4 illustrates an example relating to the information flow and operation of a system that communicates change information to client(s).
Figure 5:
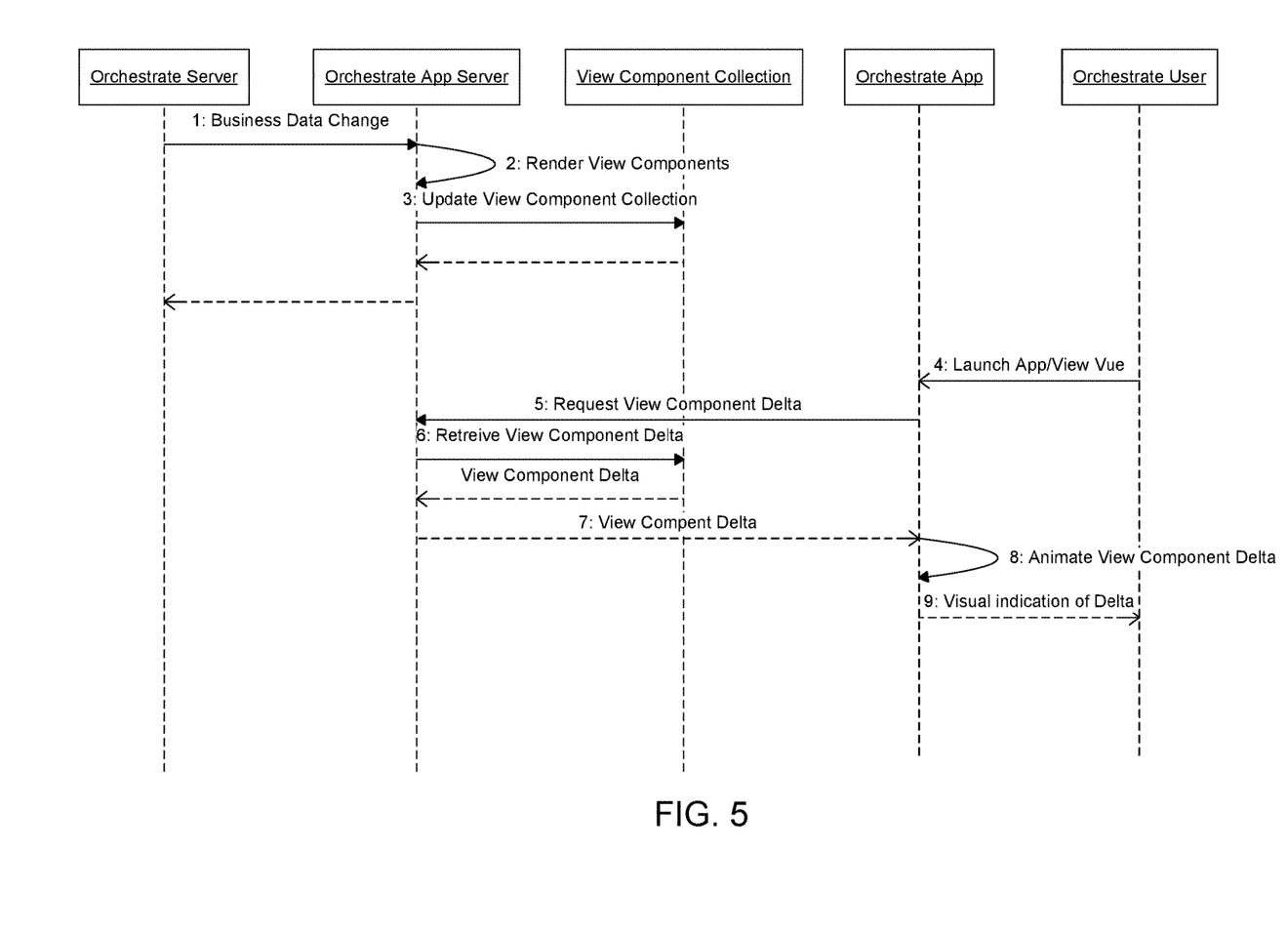
FIG. 5 illustrates an example of information flow and operation for communicating change information to clients.

Referring collectively to FIG. 4 and FIG. 5, an example embodiment is illustrated relating to the information flow and operation of a system that communicates change information to client(s), as described herein. As illustrated in this example, Orchestrate™ data (change set) arrives at the Orchestrate™ App (application) Server (UIVM Server) 403, e.g., from the Orchestrate™ server 402. This data change set is the result of an action performed within the Orchestrate™ system or as communicated thereto, e.g., by an RTLS system, a scheduling system, etc. This data reflects the current state of the Orchestrate™ system. This data is essentially used to maintain a replicated data store of the underlying Orchestrate™ database 401.

The Orchestrate™ App Server (UIVM Server) 403 uses this information to generate the view component equivalent data consumed by the Orchestrate™ client 404 (e.g., Orchestrate App of FIG. 4). This data is the presentation equivalent (e.g., rectangle position, color, pictures, strings, etc.) of the underlying Orchestrate™ data store 401.

The Orchestrate™ App Server 403 (UIVM Server) updates the current state of the view component collection. Additionally, it records this change set. At some time, the Orchestrate™ App 404 user launches the Orchestrate™ App 404 and/or selects to view the desired Orchestrate™ view. The Orchestrate™ App 404 requests the view component change set from the Orchestrate™ App Server 403 (UIVM Server) based on the view component change set sequence number it last received and processed.

Based on this sequence number, the Orchestrate™ App Server 403 (UIVM Server) retrieves all of the view component change sets the Orchestrate™ App 404 needs to reconcile its internal collection with the current state of the Orchestrate™ App Server's 403 internal collection. The view component delta or change is returned to the Orchestrate App 404. The Orchestrate App 404 updates its internal state and calculates the appropriate animations to perform (e.g., cell add, update, delete, etc.). A visual change such as a color change, appearance or modification of an icon, an animation, etc., may be used to draw attention to the Orchestrate App 1104 user to the change(s) made since the last time the data was viewed.

While the above description focuses on a mobile application/server implementation, in an embodiment, an application that is not integrated with the system may nonetheless access system data (and the various views or screens, as described further herein) by use of a web browser. This feature permits visibility to non-integrated systems (e.g., unmodified workstations and devices) with few requirements for compatibility (e.g., a workstation may need only to have a compatible web browser). This also permits a user of such a workstation or device to provide updates to the system, e.g., provided to the web browser interface and communicated to the central server.

For example, a user may operate within a web browser provided screen or view to communicate changes to the centrally managed system. For example, in a web browser, a notification (e.g., dialog box) appears when items are dragged and dropped, e.g., on to a PACU screen, to alert users that placement of the item in different screens or views or portions thereof communicates a change, e.g., moving the item into the PACU or pre-procedure section. Users may open a second instance of the application in a second browser tab or window; allowing users to have the multiple modules open at the same time.

Users may provide various inputs, e.g., into a dedicated application or a web browser view or screen, and have these inputs communicated to a central server for updates communicated across the system. For example, in a transport dialog box, a destination field may be automatically populated by the central server with a predetermined destination when patient is scheduled for a procedure, e.g., as derived from a scheduling system data set. For example, a scheduled operation that has been admitted may be designated as destined for a particular area. Users may change the automatically populated information (e.g., change destination or other information to a different location) by interfacing with the screen or view, e.g., by selecting a different destination from a list in a find location dialog box.

As may be appreciated, a variety of change data may be collected and distributed by a centralized, orchestrating system and may be made use of in a variety of ways. Particular specific example embodiments are described with respect to various implementations for improving the coordination of workflows for various service lines. Those having ordinary skill in the art will appreciate that the various examples provided herein are non-limiting and that other embodiments may fall within the scope of the claims.

A centralized manager, referred to herein as Orchestrate, coordinates information accessible from various sources, e.g., a scheduling system, an EMR system, client devices, an RTLS system, etc. As described herein, a scheduling system contains information that is scheduled to occur, whereas an EMR system provides records of what has happened. The centralized manager may improve the scheduling system by offering it additional data to improve the granularity of the scheduling system, e.g., providing the scheduling system with updates regarding staff availability, delays impacting future items in the schedule, etc. Likewise, the centralized manager may improve the quality of data in the EMR, e.g., by providing more accurate and additional information (e.g., timing information) or the like regarding procedures or events that in fact took place. By way of example, the centralized manager may enhance the value of the EMR and scheduling system by taking the anticipated schedule and tracking the workflow and procedural process in real-time from the time the workflow begins until the very end of the workflow, and sending detailed milestones to the scheduling system and/or the EMR system. This makes the scheduling data and the historical data more accurate in a real time fashion and makes this improved data available to enhance future performance.

Thus, a centralized system coordinates this information to enable staff members and support staff team members, etc., the ability to anticipate and prepare for movement from one area to another and to plan their tasks accordingly. This approach also provides views that improve transparency and anticipation of what is next in the process. Departmental and interdepartmental communications may be improved, e.g., reducing phone calls, pages, walking around and bed holds, such that the staff and other users are apprised in real time of changes to the schedule, completion of scheduled tasks or procedures, etc. The system then delivers real time updates to the schedule as changes are made and provides accurate historical data for analysis which can be used to better estimate case times, understand and eliminate bottlenecks, determine root causes of frequent delays, and improve staff utilization.

An embodiment includes a set of screens or views designed for all stakeholders in the procedural processes to communicate where a patient is at all times and what is happening as it happens. The screens share and upgrade information instantaneously across the entire system. Users can see the current patient status while management can see the entire suite and proactively address situations that may impact utilization. As will be appreciated, various views and/or versions of views may be restricted to authorized users, e.g., on the basis of login credentials and depending on the type and nature of the data contained within the screen or view.

An embodiment operates by employing templates. The templates include a set of standard screens or views for each module, which may be customized to be specific to the module (e.g., clinic, etc.) and/or by the user of the template (e.g., staff, management, patient, family, etc.). By way of non-limiting example, a template and set of screens will be described for an example work flow.

A typical patient flow may include the following. The process starts with the day's schedule being imported to a central server, e.g., from a scheduling system. This may occur for example by an embodiment employing a batch import (e.g., ASC flat file) or a real-time HL7 interface filtered for the current day with the hospital's scheduling system. The patient appears on a roster view or screen and through this screen; management of registration and admitting may take place.

The patient may then be tracked through several views or screens (or portions thereof) as they travel through the process. The views or screens may include for example views or screens appropriate for the clinic in question. Patient flow data is shared across the views or screens, e.g., as patients are moved via easy to use drag and drop functionality to different areas in a view or screen or into different views or screens. Additionally, as has been described herein, automated changes may be implemented, e.g., via RTLS data import. On such a change, e.g., a drag and drop process, the central management system may be updated such that other end clients may likewise be communicated with the retrieve or receive the change data.

Icons may graphically illustrate in the screen or view what is happening with the patient at every step of the process, e.g., displaying, changing or modifying (moving, removing, animating, etc.) of an icon may be linked with a milestone delay, completion, etc. Icons also may be used to alert and assist staff that are responsible or needed in each area. By displaying the details of what is occurring in real time, stakeholders are kept up-to-date, minimizing confusion and time wasted, e.g., with unnecessary phone calls, paging, etc. Work lists may be created to assist the staff in managing key events in the patient flow cycle.

Examples of milestones that may be monitored and utilized to communicate change data throughout the system for an example work flow are as follows. For patient arrival, a patient arrives, signs in and is admitted. The time can vary depending on if the patient was pre-registered, completed paperwork beforehand, or has special needs. Once complete, they are taken to a first area. Example milestones for this phase therefore include: patient has arrived, patient is being registered, delay(s) in registering the patient, patient registration is complete, and the patient is in the waiting area (if applicable). As described herein, an embodiment uses milestones and data related thereto (e.g., completed, pending, delayed, etc.) to produce change set data that may be communicated to various client devices such that their views or screens may be updated. The views or screens may be updated via various techniques, including the use of icons or other graphics that change in color, shape, size, etc.

Once the patient is in a first area, events take place before the patient moves to the second area. Thus, example milestones may include steps taken prior to physically moving from the first area to the second area. The actual, recorded or sensed timing data, for example reported via manual input and/or detected via automated location tracking (e.g., RFID sensors), may be compared against preexisting or predetermined milestone timing data, e.g., a predetermined schedule for when the milestones within the first area and/or transition from the first area to the second area should take place. Again, various icons may be keyed to indicate in the screen or view that the milestone(s) have or have not been achieved, as well as indicating that the milestones are partially achieved, delayed or completed ahead of time, by how long, etc.

For example, referring to FIG. 6, an embodiment provides a screen or view that includes various icons that indicate automated gap calculations based on the timing data, i.e., a delta calculated from an expected completion time, e.g., transition from a first area to a second area, and the actual completion time. In FIG. 6, the screen or view 601 may be provided to a client device or system, e.g., desktop, laptop or table computing system, smart phone or other mobile device having a display screen, etc.

The screen or view 601 illustrated in FIG. 6 lists names (e.g., patient names, clinician names, etc.), corresponding schedules, and predicted/predetermined milestone timing, i.e., scheduling data, generally indicated at 602. As may be appreciated by reviewing the enlargement of the screen or view indicated at 603, the screen or view 601 includes a color coded icon (here, a color coded rectangular box 604) that indicates that the patients are currently ahead of schedule. Likewise, the screen or view 601 includes a color coded graphic 605 (e.g., green for ahead of schedule, that is a milestone has completed ahead of a predicted schedule time), indicating a gap (extra time) in the schedule (generally indicated at 602).

Such milestones may be used as points at which updates within the centrally managed system are provided. For example, on reaching a predetermined milestone time, for example as programmed in the system, the fact that a milestone has or has not been achieved, e.g., via input interface of an end user, RTLS data, etc., the system may generate a milestone indicator, which then may be communicated to various client devices, e.g., by updating an icon display in a view or screen to show the completed milestone, its progression stage towards completion, its early completion, its delay, etc.

Figure 7:
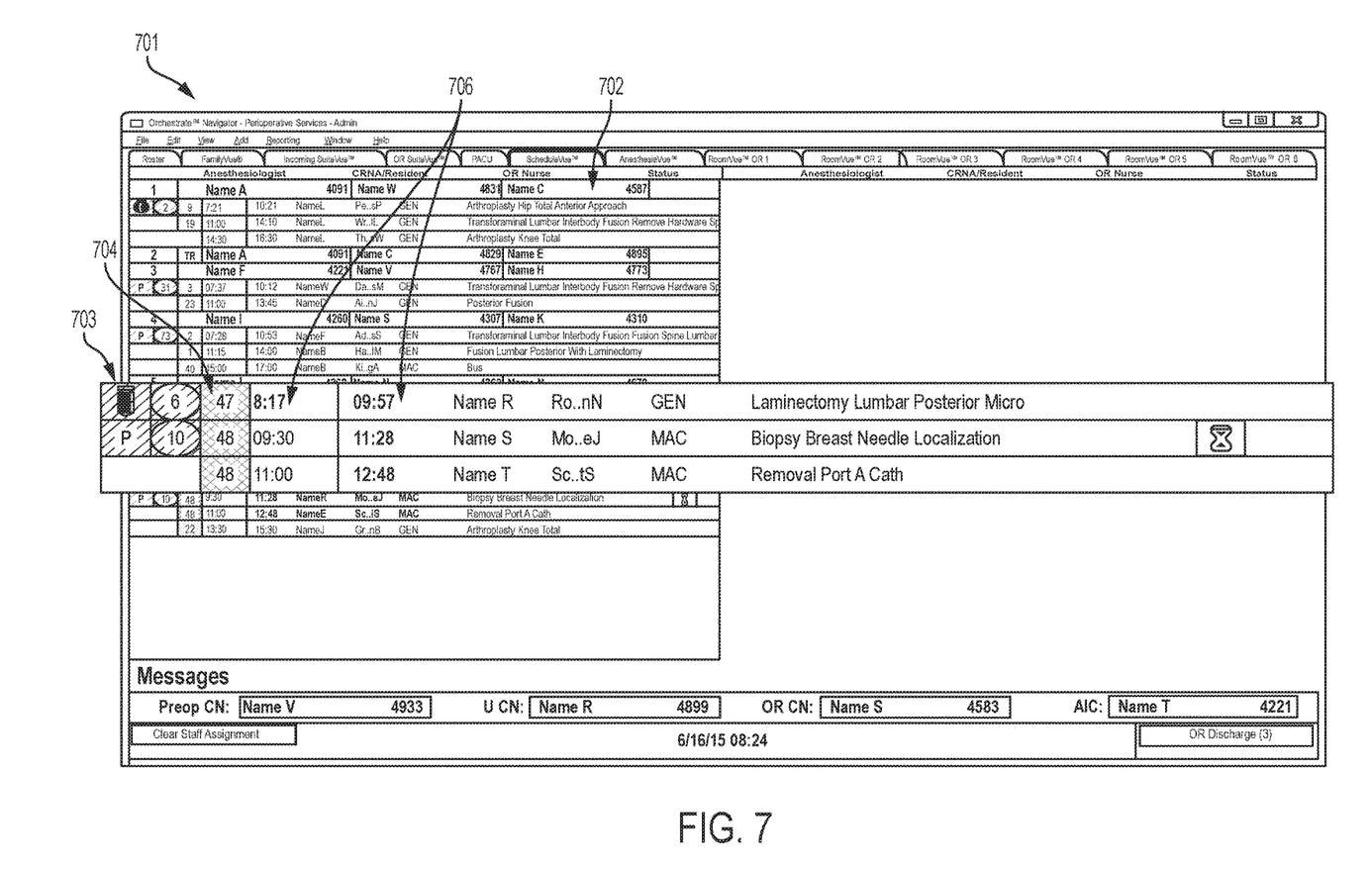
FIG. 7 illustrates an example user interface displaying overlap change information on a client display device.

Likewise, a screen or view 701 illustrated in FIG. 7 provides information, retrieved from a centralized system and displayed locally at a client, indicating that overlaps have occurred, i.e., scheduled procedures are taking longer to complete than predicted. For example, in the screen or view 701, it can be appreciated that different color coding (as compared to FIG. 6, element 604) is used in a graphical element 704 of the screen or view to indicate that patients are behind schedule, illustrated generally at 702. It may further be appreciated in the enlarged view illustrated at 703 that three patients are behind schedule, indicated by a graphic 704 with appropriate color coding indicating that an overlap is likely (i.e., the currently scheduled event will last longer than a predicted time, and thus will run into or overlap with another, upcoming scheduled event). The actual time it has taken or the extra time it is taking to complete the procedure may be visually indicated, e.g., with a color coded timing graphic 706. This alters the staff to the fact that a delay has been sensed or recorded, and the delay is reported simultaneously to multiple client devices. With the reporting of the actual timing data 706, the size or magnitude of the delay is communicated in near real time to the client device(s).

An embodiment is positioned as a centralized service and provides interface capability with hospital/clinic scheduling and clinical systems for an integrated platform to optimize efficiency in procedural care areas. An embodiment may for example utilize HL7 standards as a common framework for integration with external systems. Scheduling messages sent to an embodiment may include new, modified, and rescheduled cases as well as appointment cancellations. Scheduling information may be used to populate an embodiment database with the current day's schedule and this data store may be updated throughout the day, e.g., based on messages from the hospital/clinic scheduling system. Scheduled appointments for future dates may be stored and presented on the appropriate day within the various views or screens, as described herein.

Figure 8:
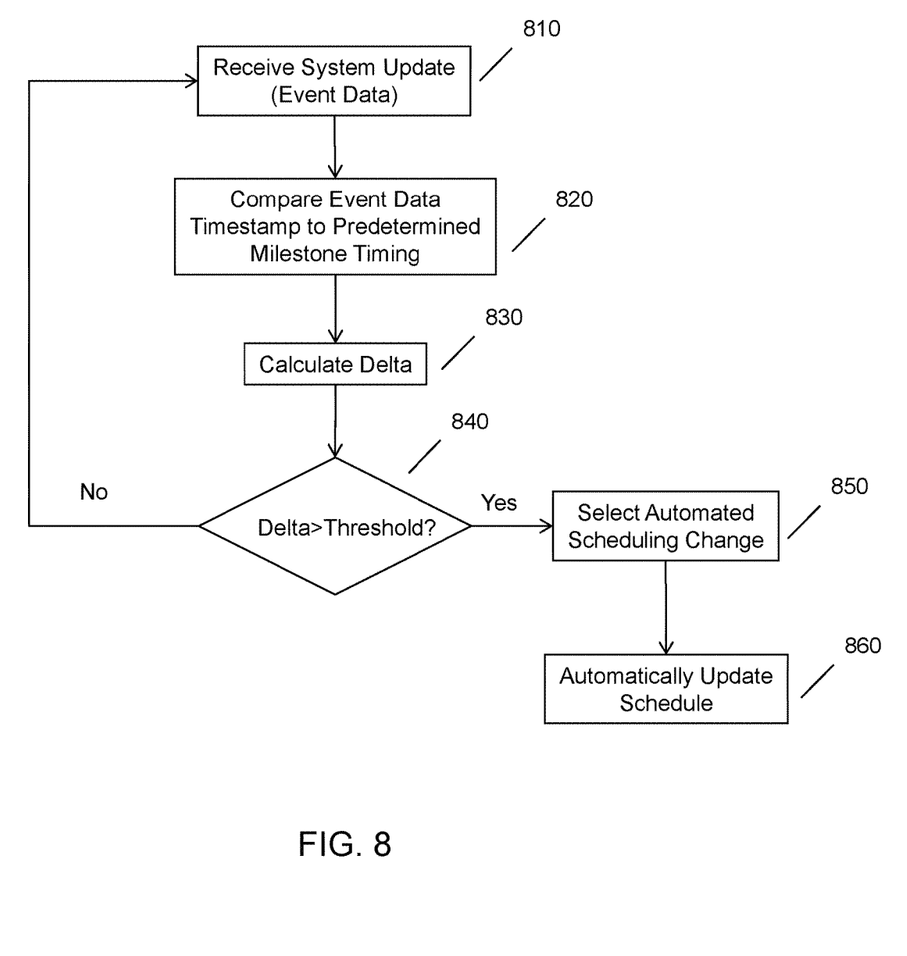
FIG. 8 illustrates an example method of automated scheduling changes implemented in response to change information.

For example, and referring to FIG. 8, an example method of automated scheduling changes is illustrated. As event data becomes available from the system, e.g., a predetermined milestone has been completed, has been missed, etc., an embodiment receives the event data, as illustrated at 810. The event data includes a timestamp, i.e., a time at which the event was recorded. The event data timestamp is compared to a predetermined milestone timing at 820. This permits an embodiment to determine or calculate a delta, i.e., a difference between the timestamp of the event data and the predetermined timing, as illustrated at 830.

If the delta exceeds a threshold, e.g., the actual timing data of the event is more than a predetermined amount different that the expected timing thereof, an embodiment may produce an action item, e.g., selecting an automated scheduling change, as illustrated at 850. For example, an embodiment may notice that a procedure is taking longer than expected; based on the magnitude of the delay, an embodiment may select to move of change a following or upcoming event (e.g., next step in the procedure, next patient to enter the current step, etc.). Similar automated changes may be selected for deltas that indicate a procedure step is moving more quickly through a process.

Having determined a scheduling change, an embodiment may automatically modify or propose a modification to the schedule, as illustrated at 860. This permits any dependent or related procedure steps and/or procedures to be adjusted (e.g., re-routed) as necessary based on real time event data input.

Thus, an embodiment may send and receive information, e.g., via HL7 messages, for specific real-time events, for example including milestones and patient movement in the procedural care areas. If a facility has an existing information system or RTLS service with patient flow data available, an embodiment may be used to improve the granularity or detailed milestones of the existing modules. For example, even if an existing system does have a procedural flow capability, it may not be integrated across the whole facility and have access to various systems, thereby only providing limited value. Additionally, existing systems do not have the reporting and scheduling capability to use the existing data, e.g., for longer term improvements.

An embodiment may be integrated with an RTLS to automate the manual progression of location based milestones (e.g., automate a "drag and drop" function performed by staff in a screen or view), such as patient moves. RTLS integration may reduce manual intervention and eliminate errors, increase compliance within the system, decrease delays, and provide accurate time stamps of events automatically. As may be appreciated, this frees staff to focus on the job at hand.

RTLS integration provides improved workflow by automatically detecting patient or asset location and triggering milestones, eliminating manual updates and reduced the potential for human error. Additionally, automated patient location and movement of staff, patients and equipment resources may be communicated throughout the system, e.g., by a central manager communicating updates automatically, e.g., via change set data distributed to a requesting client device.

As will be appreciated by one skilled in the art, various aspects may be embodied as a system, method or device program product. Accordingly, aspects may take the form of an entirely hardware embodiment or an embodiment including software that may all generally be referred to herein as a "circuit," "module" or "system." Furthermore, aspects may take the form of a device program product embodied in one or more device readable medium(s) having device readable program code embodied therewith.

Any combination of one or more non-signal device readable storage medium(s) may be utilized. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a storage medium is not a signal and "non-transitory" includes all media except signal media.

Program code embodied on a storage medium may be transmitted using any appropriate medium, including but not limited to wireless, wireline, optical fiber cable, RF, et cetera, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of connection or network, including a local area network (LAN) or a wide area network (WAN), or the connection may be made through other devices (for example, through the Internet using an Internet Service Provider), through wireless connections, e.g., near-field communication, or through a hard wire connection, such as over a USB connection.

Example embodiments are described herein with reference to the figures, which illustrate example methods, devices and program products according to various example embodiments. It will be understood that the actions and functionality may be implemented at least in part by program instructions. These program instructions may be provided to a processor of a special purpose information handling device or other programmable data processing device to produce a machine, such that the instructions, which execute via a processor of the device implement the functions/acts specified.

It is worth noting that while specific blocks (or other illustrated elements or text) are used in the figures, and a particular ordering of blocks has been illustrated, these are non-limiting examples. In certain contexts, two or more blocks may be combined, a block may be split into two or more blocks, or certain blocks may be re-ordered or re-organized as appropriate, as the explicit illustrated examples are used only for descriptive purposes and are not to be construed as limiting.

As used herein, the singular "a" and "an" may be construed as including the plural "one or more" unless clearly indicated otherwise.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A method, comprising:
   communicating with a server to obtain a set of event data, said set of event data comprising timestamped event data;
   automatically determining, using a processor and without additional user input, a delta between said set of event data and a predetermined scheduling milestone;
   identifying, using a processor, a display element impacted by the delta; and
   updating, using the processor, the display element according to the delta;
   said updating comprising changing a color of a display graphic in a schedule view to visually indicate the delta, said color being dependent on the delta with respect to a predetermined time threshold.

2. The method of claim 1, wherein the display graphic is a bar graphic occupying a slot of a schedule.

3. The method of claim 2, wherein the display graphic is a numeric graphic.

4. The method of claim 3, further comprising automatically identifying, using the processor, a schedule change based on the delta.

5. The method of claim 4, further comprising implementing the schedule change.

6. The method of claim 5, wherein the implementing is automated using the processor.

7. The method of claim 5, wherein the schedule change is selected from a group of predefined scheduling changes.

8. The method of claim 6, wherein each of the group of predefined scheduling changes is associated with a particular delta.

9. The method of claim 1, wherein the event data comprises real time location data derived from an RFID tracking device.

10. The method of claim 1, wherein the event data data comprises manual input data derived from a client device.

11. A system, comprising:
   a memory storing instructions;
   a processor configured to execute the instructions to:
   communicate with a server to obtain a set of event data, said set of event data comprising timestamped event data;
   automatically determine, without additional user input, a delta between said set of event data and a predetermined scheduling milestone;
   identify a display element impacted by the delta; and
   update the display element according to the delta;
   said update comprising changing a color of a display graphic in a schedule view to visually indicate the delta, said color being dependent on the delta with respect to a predetermined time threshold.

12. The system of claim 11, wherein the display graphic is a bar graphic occupying a slot of a schedule.

13. The system of claim 12, wherein the display graphic is a numeric graphic.

14. The system of claim 13, wherein the processor further automatically identifies a schedule change based on the delta.

15. The system of claim 14, wherein the processor further implements the schedule change.

16. The system of claim 15, wherein the schedule change is automated using the processor.

17. The system of claim 15, wherein the schedule change is selected from a group of predefined scheduling changes.

18. The system of claim 16, wherein each of the group of predefined scheduling changes is associated with a particular delta.

19. The system of claim 11, wherein the event change data comprises real time location data derived from an RFID tracking device.

20. A program product, comprising:
   a storage device having code stored therein that is executable by a processor, the code comprising:
   code that communicates with a server to obtain a set of event data said set of event data comprising timestamped event data;
   code that automatically determines a delta between said set of event data and a predetermined scheduling milestone;
   code that identifies, using a processor, a display element impacted by the delta; and
   code that updates, using the processor, the display element according to the delta;
   said update comprising changing a color of a display graphic in a schedule view to visually indicate the delta, the color being dependent on the delta with respect to a predetermined time threshold.

* * * * *